United States Patent [19]

Pivawer et al.

[11] 3,987,129
[45] Oct. 19, 1976

[54] PROCESS FOR PREPARING BIS(2-HALOALKYL) PHOSPHORO-HALIDATES

[75] Inventors: Philip M. Pivawer, Hamden, Conn.; Adrian D'Souza, Lake Charles, La.; Joseph J. Levitzky, Hamden, Conn.

[73] Assignee: Olin Corporation, New Haven, Conn.

[22] Filed: Feb. 26, 1975

[21] Appl. No.: 553,268

[52] U.S. Cl. .............................. 260/986; 260/977
[51] Int. Cl.² ........................................ C07F 9/14
[58] Field of Search ............... 260/986, 977, 960

[56] References Cited
UNITED STATES PATENTS

| | | |
|---|---|---|
| 3,803,272 | 4/1974 | Pivawer et al. ............... 260/977 X |
| 3,810,961 | 5/1974 | Pivawer ............................ 260/977 |
| 3,886,239 | 5/1975 | Pivawer ............................ 260/977 |

*Primary Examiner*—Richard L. Raymond
*Attorney, Agent, or Firm*—F. A. Iskander; T. P. O'Day

[57] ABSTRACT

An improved process is disclosed for the preparation of bis(2-haloalkyl) phosphorohalidates. This process comprises the steps of reacting phosphorus trihalide with a stoichiometric excess of alkylene oxide to form tris(2-haloalkyl) phosphite, substantially eliminating the presence of unreacted alkylene oxide in the tris(2-haloalkyl) phosphite, and finally converting it to bis(2-haloalkyl) phosphorohalidate by reaction with halogen.

13 Claims, No Drawings

PROCESS FOR PREPARING BIS(2-HALOALKYL) PHOSPHORO-HALIDATES

This invention relates to an improved process for the preparation of bis(2-haloalkyl) phosphorohalidates which are represented by the formula

$$XP(OCH_2CHX)_2 \quad \text{with } \|O \text{ and } R$$

wherein X represents a halogen and R represents hydrogen or an alkyl group of 1 to 6 carbon atoms.

The bis(2-haloalkyl) phosphorohalidates of formula I are known to be valuable chemical intermediates for use in the preparation of flame retarding additives. For example, they react with alkylene glycols to form tetrakis(2-haloalkyl) alkylene diphosphates, which are useful as additives for reducing the flammability of polyurethane foam. See U.S. Pat. No. 3,707,586.

According to the prior art, the bis(2-haloalkyl) phosphorohalidates can be prepared by a two-step process wherein phosphorus trihalide is reacted with an alkylene oxide to form tris(2-haloalkyl) phosphite, the product of this reaction being then reacted with a halogen to convert the tris(2-haloalkyl) phosphite to bis(2-haloalkyl) phosphorohalidate. See U.S. Pat. Nos. 3,803,272 and 3,810,961. It is also known in this art that in the reaction of phosphorus trihalide with alkylene oxide, it is advantageous to use a stoichiometric excess of alkylene oxide in order to avoid undesirable side reactions and achieve full utilization and conversion of the phosphorus trihalide. Thus the product of the phosphorus trihalide oxyalkylation reaction, which is subsequently subjected to halogenation, is usually comprised of tris(2-haloalkyl) phosphite and varying proportions of unreacted alkylene oxide.

It has now been found that the use of excess alkylene oxide, while essential to optimizing the oxyalkylation of phosphorus trihalide, has one drawback. This is that when the product phosphite, containing unreacted alkylene oxide, is subsequently reacted with halogen to form bis(2-haloalkyl) phosphorohalidate, an undesirable side reaction takes place, the net effect of which is to reduce the yield of phosphorohalidate. This side reaction, which is caused by the presence of, and involves, alkylene oxide, results in the partial conversion of the bis(2-haloalkyl) phosphorohalidate to tris(2-haloalkyl) phosphate.

Thus pursuant to the invention, an improved process is provided for the preparation of bis(2-haloalkyl) phosphorohalidate, whereby the formation of tris(2-haloalkyl) phosphate is minimized and a maximum yield of product is provided. Broadly speaking, this objective is achieved in the process of the invention by the intermediate step of substantially reducing or eliminating the presence of unreacted alkylene oxide in the tris(2-haloalkyl) phosphite intermediate before this is subjected to halogenation.

Any suitable expedient or method may be used to reduce or eliminate the presence of unreacted alkylene oxide in the tris(2-haloalkyl) phosphite intermediate such as stripping or vacuum distillation. However, in accordance with the preferred embodiments of the invention, which are described in detail hereinbelow, the substantial elimination of unreacted alkylene oxide is achieved in a selective, continuous process for preparing bis(2-haloalkyl) phosphorohalidate. In this process, substantially all of the unreacted alkylene oxide is reacted with about a stoichiometric proportion of phosphorus trihalide, this reaction being effected in a separate or post oxyalkylation reactor.

More in detail, in its preferred embodiments the process of the invention comprises the following continuous steps:

a. in a first reaction zone, reacting phosphorus trihalide with a stoichiometric excess of alkylene oxide to form a product comprised of tris(2-haloalkyl) phosphite and unreacted alkylene oxide, b. transferring the product of step (a) to a second reaction zone and reacting substantially all of the unreacted alkylene oxide therein with about a stoichiometric proportion of phosphorus trihalide, thereby converting substantially all of the unreacted alkylene oxide to tris(2-haloalkyl) phosphite, and c. in a third reaction zone, reacting the tris(2-haloalkyl) phosphite formed in steps (a) and (b) with halogen thereby converting it to bis(2-haloalkyl) phosphorohalidate.

The reaction of the phosphorus trihalide with the alkylene oxide can be represented by equation II as follows:

$$PX_3 + 3CH_2CHR \longrightarrow P(OCH_2CHX)_3 \quad \text{II}$$

in which X and R have the significance indicated above.

In carrying out this reaction it is contemplated that any phosphorus trihalide may be employed, i.e., X can be chlorine, bromine, iodine or fluorine. However, it is preferred to employ those phosphorus trihalides in which the halogen is chlorine or bromine. The use of phosphorus trichloride is particularly preferred.

The alkylene oxide which is reacted with the phosphorus trihalide can be any alkylene oxide having a 1,2-epoxide ring and from 2 to 8 carbon atoms. Illustrative are ethylene oxide, propylene oxide, butylene oxide, pentylene oxide, ephichlorohydrin, trichlorobutylene oxide, hexylene oxide, octylene oxide, and the like. The preferred alkylene oxides are those having 2–4 carbon atoms, ethylene oxide being most preferred.

As indicated above a stoichiometric excess of alkylene oxide is employed in the oxyalkylation of phosphorus trihalide. Such excess may vary over a wide range such as from about 3.02 to about 10, and preferably about 3.05–6, moles of alkylene oxide per each mole of phosphorus trihalide. The reaction is preferably carried out in the presence of a tertiary amine hydrohalide catalyst, the tertiary amine hydrochlorides being particularly preferred. Such catalysts and their use in the oxyalkylation reaction are described in detail in U.S. Pat. No. 3,810,961 which issued to P. M. Pivawer on May 14, 1974. The entire disclosure of this patent is incorporated herein by reference.

The reaction of the phosphorus trihalide with the alkylene oxide may be carried out in the presence or absence of a solvent medium. However, the use of a solvent is preferred. For this purpose any inert organic liquid may be employed provided it is a solvent for both the catalyst and the phosphorus trihalide reactant. Ethylene dichloride is a particularly preferred solvent and this can be used in any suitable proportion such as about 50–1,000 parts by weight per every 100 parts of the combined weight of phosphorus trihalide and alkylene oxide. It is also preferred to carry out the reaction in the absence of moisture. Any suitable means, such as the use of a blanket of nitrogen gas, may be employed for this purpose.

The oxyalkylation of phosphorus trihalide may be carried out in any suitable type of reactor. Usually a conventional reactor is used which is equipped with an agitator, a recording thermometer and a heat transfer element for maintaining the reactor contents at the desired reaction temperature. Any convenient order of continuously supplying the reactants may be employed. However, it is generally preferred to simultaneously feed the reactants, catalyst and solvent, if such are used, to the reactor which is maintained in constant agitation and preferably at a temperature of about 50°–115° C and more preferably about 80°–110° C. The pressure under which the reaction is carried out is not critical. Thus any suitable reaction pressure may be used. However, for reasons of economy and convenience, it is preferred to operate at about atmospheric pressure. It is also preferable to carry out the oxyalkylation reaction under reflux conditions which can be accomplished by the simple conventional expedient of fitting the reactor with a reflux condenser. The use of reflux is advantageous for two reasons. One is that it is conducive to easy temperature control by removal of heat of reaction via reflux condensation. Secondly, it enables the removal of part, but not all, of the excess alkylene oxide in the form of gas which optionally may be condensed and recycled to the reactor. It is to be noted, however, that it is not possible to remove all of the excess alkylene oxide by refluxing. Thus so long as excess alkylene oxide is used, a proportion of that excess will become trapped or dissolved in the liquid oxyalkylation reaction product regardless of whether or not the reaction is carried out under reflux conditions.

In the continuous operation of the phosphorus trihalide oxyalkylation reactor, the rates of reactants feed and product withdrawal are regulated so as to maintain the desired level of reaction mixture inside the reactor while at the same time insuring the requisite residence time which is necessary for complete reaction and conversion of the phosphorus trihalide. Such residence time usually is at least about 20, and preferably about 25–120, minutes. The product of the reaction, which is continuously withdrawn from the reactor, will be a mixture comprised of tris(2-haloalkyl) phosphite and unreacted alkylene oxide, along with catalyst and solvent if such are used.

Pursuant to the invention, the product of the reaction of phosphorus trihalide with excess alkylene oxide is continuously fed to a second or post reactor to which further amounts of phosphorus trihalide are supplied for reaction with the unreacted alkylene oxide. By using this post reactor, which may be of the same type as the first or main oxyalkylation reactor, several benefits are realized according to the invention. First full utilization of the alkylene oxide, which is used in the main oxyalkylation reactor, is achieved. Secondly, and more importantly, an oxyalkylation product is obtained, for use in making bis(2-haloalkyl) phosphorohalidate, which is free of unreacted alkylene oxide. This in turn means prevention of undesirable side reactions, during the subsequent halogenation reaction, which would otherwise result in the partial conversion of bis(2-haloalkyl) phosphorohalidate to tris(2-haloalkyl) phosphate. Thirdly, this objective is achieved in a continuous and efficient operation which precludes interruption of the main oxyalkylation reaction and avoids wasting phosphorus trihalide.

For most efficient utilization of the post reactor, which is operated under substantially the same conditions as the first reactor, the feed of phosphorus trihalide thereto is regulated depending on the content of unreacted alkylene oxide in the feed which is supplied from the first reactor. To this end, this alkylene oxide content is periodically or continuously monitored, using conventional analytical techniques; and the continuous addition of phosphorus trihalide is closely controlled to provide approximately the stoichiometric amount which is required to react with the analyzed unreacted alkylene oxide. Thus for example, for every mole of unreacted alkylene oxide which is indicated by analysis of the first reactor output, about one-third of a mole of phosphorus trihalide is added to the post reactor. In actual continuous operation of the first reactor, wherein uniform rates of reactants feed and product withdrawal are maintained, the proportion of unreacted alkylene oxide in the output of that reactor which is fed to the post reactor will become fairly uniform after a few hours of operation. Thus from that point forward, it becomes a routine matter to continuously feed into the post reactor, at a constant pre-calculated rate, the requisite proportion of phosphorus trihalide that is needed to consume substantially all of the unreacted alkylene oxide. Nevertheless analysis for unreacted alkylene oxide in the post reactor output should be made periodically, so that if necessary appropriate adjustment can be made in the feed rate of phosphorus trihalide in order to prevent waste of this material on the one hand, or, on the other hand to make sure that practically all of the unreacted alkylene oxide is converted to tris(2-haloalkyl) phosphite.

The output of the post reactor, which is substantially free, or contains a negligible amount, e.g., less than 0.2% by weight, of unreacted alkylene oxide, will be comprised of tris(2-haloalkyl) phosphite along with catalyst and solvent if such are used in the first reactor. This output is continuously fed to a third reactor in which the tris(2-haloalkyl) phosphite is converted to bis(2-haloalkyl) phosphorohalidate by reaction with a halogen. This reaction is represented by equation III as follows:

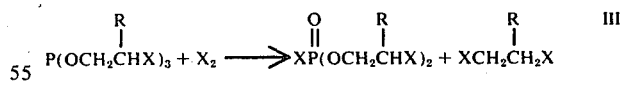

wherein R and X have the significance indicated above.

The halogen which is employed in this reaction can be in the liquid or gaseous state, the latter being preferred. Although it is contemplated that any halogen may be employed as a reactant, it is preferred to employ chlorine or bromine, chlorine being particularly preferred.

Any suitable molar ratio of halogen to phosphite may be employed in carrying out the phosphorohalidate-forming reaction. For example, stoichiometric proportions can be used. However, it is preferred according to the invention to employ a stoichiometric excess of halogen, such as from about 1.01 to about 1.3 times the amount which is stoichiometrically required to react with the tris(2-haloalkyl) phosphite. The use of such excess, while insuring completion of the reaction, has no detrimental effect on the reaction product. The use of such an excess, furthermore, provides a practically easy means of ascertaining that all of the phosphite has been reacted. This is by virtue of the fact that a simple color signal, e.g., yellow color where the halogen reactant is chlorine, is provided by the presence of excess halogen in the third reactor output, which indicates complete reaction and conversion of the tris(2-haloalkyl) phosphite.

The halogenation reaction is effected in a third reactor which may be of a conventional type such as used in the oxyalkylation of phosphorus trihalide. To this reactor, the output of the post reactor is transferred on a continuous basis. The halogen reactant is charged to the reactor as a separate stream.

The halogenation reaction is effected at any suitable temperature and pressure within the third reactor. However, it is preferred to employ atmospheric pressure and a temperature of about 0°–130° C and still more preferably about 30°–115° C. It is also preferred to carry out the halogenation reaction under reflux conditions which are conducive to easy temperature control and to the simplified removal of excess halogen.

The reactants feed rate and the rate of product withdrawal are regulated so as to maintain the desired level in the third reactor while insuring the requisite reactants residence time, usually about 5–120 minutes, which is necessary for complete reaction and conversion of the tris(2-haloalkyl) phosphite to bis(2-haloalkyl) phosphorohalidate.

The product that is withdrawn from the third reactor is a mixture comprised of bis(2-haloalkyl) phosphorohalidate and alkylene dihalide, along with catalyst and solvent if such are used in the oxyalkylation of phosphorus trihalide and are not subsequently removed before effecting the halogenation reaction. As such, this mixture can be utilized directly, by reacting the bis(2-haloalkyl) phosphorohalidate therein with an alkylene glycol, in the preparation of tetrakis(2-haloalkyl) alkylene diphosphate. However, if desired, the bis(2-haloalkyl) phosphorohalidate in the mixture may be recovered in concentrated or purified form. To this end, conventional recovery and purification techniques may be used such as vacuum distillation.

The improved process of the invention enables the preparation of bis(2-haloalkyl) phosphorohalidate which is substantially free of tris(2-haloalkyl) phosphate impurity. Furthermore, this objective of the invention is achieved by a relatively simple and economically attractive, continuous method which minimizes waste and optimizes the purity and yield of bis(2-haloalkyl) phosphorohalidate product.

The following examples are provided to illustrate the invention. In these examples, all parts and percentages are by weight unless otherwise specified.

EXAMPLE 1

A. Preparation of Tris(2-chloroethyl) Phosphite

The continuous preparation of tris(2-chloroethyl) phosphite was carried out in a conventional, continuous-flow, stirred tank reactor having two side inlets and a bottom outlet. The reactor was fitted with a thermometer and a reflux condenser.

Through one reactor inlet there were charged 1518 grams of an ethylene dichloride solution containing 759 grams of phosphorus trichloride and 2.9 grams of pyridine hydrochloride catalyst. Through the other reactor inlet 955 grams of ethylene oxide were charged. As the exothermic reaction of ethylene oxide and phosphorus trichloride proceeded, the temperature inside the reactor began to rise reaching a stable level within the range of about 100°–105° C. During the course of reaction part of the excess ethylene oxide present was vaporized and removed via the reflux condenser. After a residence time of about 50 minutes, continuous feeding of additional amounts of reactants, solvent and catalyst was commenced with simultaneous removal of reactor output through the bottom outlet. The reactor feed rate was maintained at 955 grams of ethylene oxide and 1518 grams of ethylene dichloride-phosphorus trichloride-catalyst solution per hour; and the output withdrawal was maintained at 2270 grams per hour.

The product withdrawn from the reactor was periodically analyzed by vapor phase chromatography (VPC) and nuclear magnetic resonance (NMR). The results of the analyses, which were essentially the same throughout a continuous 12-hour run, were as follows:

64% tris(2-chloroethyl) phosphite
34.9% ethylene dichloride
1.04% ethylene oxide (23.6 grams per hour)
0.13% pyridine hydrochloride catalyst (calculated)

B. Conversion of Unreacted EO to Phosphite

The product withdrawn from the ethoxylation reactor was directly and continuously fed to a second or post reactor which was simultaneously charged with a 50% solution of phosphorus trichloride in ethylene dichloride at the continuous rate of 50 grams of solution per hour. The post reactor was of the same design as the ethoxylation reactor, but it was not fitted with a reflux condenser and the temperature of the interior thereof was maintained at 50° C. Continuous withdrawal of product from the post reactor was carried out at the rate of 2320 grams per hour, which rate was calculated to allow for a residence time of approximately 13 minutes while maintaining a constant liquid level.

The product withdrawn from the post reactor was periodically analyzed by VPC for unreacted ethylene oxide which was found to be negligible (i.e., below 0.1%).

C. Preparation of Bis(2-chloroethyl) Phosphorochloridate

The continuous conversion of tris(2-chloroethyl) phosphite to bis(2-chloroethyl) phosphorochloridate was performed in a reflux chlorination reactor which was identical to the ethoxylation reactor. The post reactor output was directly charged to the chlorination reactor which was maintained at 95°–100° C. Simultaneously, gaseous chlorine was charged at the constant rate of 516 grams per hour. Continuous operation, i.e., continuous feed and product discharge, was commenced at the same rate after an initial residence time of 32 minutes. NMR analysis of the product which was continuously recovered from the chlorination reactor indicated that over 98% of the phosphorus in this product was in the form of bis(2-chloroethyl) phosphorochloridate. The balance of the phosphorus, i.e., under 2%, was in the form of tris(2-chloroethyl) phosphate.

Comparison 1

The continuous preparation of bis(2-chloroethyl) phosphorochloridate was carried out, following prior art methods wherein, except for the absence of the post reaction step, essentially the same procedure and relative proportions of reactants were used as described in Example 1. The product, upon analysis by NMR, was found to contain varying proportions of tris(2-chloroethyl) phosphate ranging from 7 to 10% based. This comparison demonstrates the criticality of using a phosphorus trichloride-ethylene oxide post reactor, as taught according to the invention, in order to reduce or prevent the formation of tris(2-chloroethyl) phosphate and thereby maximize the yield of tris(2-chloroethyl) phosphite.

What is claimed is:

1. A continuous process for preparing bis(2-haloalkyl) phosphorohalidate of the formula

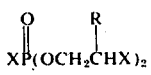

wherein X is a halogen selected from chlorine and bromine and R is hydrogen or an alkyl radical having 1–6 carbon atoms, which process comprises:
 a. in a first reaction zone reacting, in the presence of a tertiary amine hydrohalide catalyst, phosphorus trihalide, in which the halogen is chlorine or bromine, with a stoichiometric excess of an alkylene oxide having a 1,2-epoxide ring and 2–8 carbon atoms, thereby forming a first product mixture comprised of tris(2-haloalkyl) phosphite and unreacted alkylene oxide,
 b. transferring said first product mixture to a second reaction zone and reacting substantially all of said unreacted alkylene oxide therein with about a stoichiometric proportion of phosphorus trihalide thereby forming a second product mixture, comprised of tris(2-haloalkyl) phosphite, which is substantially free of unreacted alkylene oxide, and
 c. in a third reaction zone, reacting said tris(2-haloalkyl) phosphite, as formed in steps (a) and (b), with a halogen selected from chlorine and bromine thereby converting said tris(2-haloalkyl) phosphite to bis(2-haloalkyl) phosphorohalidate.

2. A process, as claimed in claim 1, for preparing bis(2-chloroethyl) phosphorochloridate wherein said phosphorus trihalide is phosphorus trichloride, said alkylene oxide is ethylene oxide, said tris(2-haloalkyl) phosphite is tris(2-chloroethyl) phosphite, and said halogen is chlorine.

3. The process of claim 2 wherein said tertiary amine hydrohalide is pyridine hydrochloride and the reaction of step (a) is carried out in the presence of ethylene dichloride solvent.

4. The process of claim 1 wherein the reactions of steps (a) and (b) are carried out at a temperature of about 50°–115° C and the reaction of step (c) is carried out at a temperature of about 0°–130° C.

5. The process of claim 4 wherein a stoichiometric excess of said halogen is used in step (c).

6. The process of claim 5 wherein the reaction of step (a) is carried out using 3.02–10 moles of said alkylene oxide per every mole of said phosphorus trihalide.

7. The process of claim 6 wherein said alkylene oxide contains 2–4 carbon atoms.

8. A process, as claimed in claim 7, for preparing bis(2-chloroethyl) phosphorochloridate wherein said phosphorus trihalide is phosphorus trichloride, said alkylene oxide is ethylene oxide, said tris(2-haloalkyl) phosphite is tris(2-chloroethyl) phosphite, and said halogen is chlorine.

9. The process of claim 8 wherein the reaction of step (a) is carried out in the presence of an inert solvent medium and under reflux conditions.

10. The process of claim 9 wherein said tertiary amine hydrohalide is pyridine hydrochloride and said inert solvent is ethylene dichloride.

11. The process of claim 10 wherein the reactions of steps (a) and (b) are carried out at a temperature of about 80°–110° C.

12. The process of claim 11 wherein the reaction of step (a) is carried out at atmospheric pressure using about 3.05–6 moles of ethylene oxide per mole of phosphorus trichloride.

13. The process of claim 12 wherein the reaction of step (c) is carried out at about 30°–115° C, under reflux conditions, and using a proportion of chlorine which is about 1.01–1.3 times that which is stoichiometrically required to react with said tris(2-chloroethyl) phosphite.

* * * * *